(12) United States Patent
Carr, Jr. et al.

(10) Patent No.: US 7,060,103 B2
(45) Date of Patent: *Jun. 13, 2006

(54) TISSUE REPAIR FABRIC

(75) Inventors: Robert M. Carr, Jr., West Roxbury, MA (US); Kimberlie D. Condon, Brant Rock, MA (US); Paul L. Termin, St. Paul, MN (US); Janet Hardin Young, Cary, NC (US)

(73) Assignee: Organogenesis Inc., Canton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/376,788

(22) Filed: Feb. 28, 2003

(65) Prior Publication Data

US 2003/0158607 A1 Aug. 21, 2003

Related U.S. Application Data

(63) Continuation of application No. 09/843,172, filed on Apr. 26, 2001, now abandoned, which is a continuation-in-part of application No. 08/930,756, filed on Oct. 7, 1997, now abandoned, which is a continuation-in-part of application No. PCT/US96/03336, filed on Mar. 12, 1996, which is a continuation-in-part of application No. 08/417,868, filed on Apr. 7, 1995, now Pat. No. 5,733,337.

(51) Int. Cl.
*A61F 2/02* (2006.01)

(52) U.S. Cl. .................. 623/23.72; 623/1.44; 623/915; 623/917; 606/151

(58) Field of Classification Search ................. 623/1.1, 623/1.44, 1.47, 1.5–1.54, 11.11, 23.72–23.76, 623/915, 917, 920, 921; 606/151
See application file for complete search history.

(56) References Cited

U.S. PATENT DOCUMENTS

| | | | |
|---|---|---|---|
| 2,127,903 A | 8/1938 | Bowen | |
| 3,272,204 A | 9/1966 | Artandi et al. | |
| 3,329,572 A | 7/1967 | Malgouzou | |
| 3,366,440 A | 1/1968 | Nuwayser | 8/115.6 |
| 3,551,560 A | 12/1970 | Thiele | |
| 3,562,820 A | 2/1971 | Braun | |
| 3,914,802 A | 10/1975 | Reick | |
| 3,919,411 A * | 11/1975 | Glass et al. | 424/78.27 |
| 3,974,526 A | 8/1976 | Dardik et al. | |
| 4,082,507 A | 4/1978 | Sawyer | |
| 4,148,664 A * | 4/1979 | Cruz, Jr. | 602/50 |
| 4,252,759 A | 2/1981 | Yannas | |
| 4,319,363 A | 3/1982 | Ketharanathan | |
| 4,323,525 A | 4/1982 | Bornat | |
| 4,378,224 A | 3/1983 | Nimni et al. | |
| 4,420,339 A | 12/1983 | Kato | |
| 4,475,972 A | 10/1984 | Wong | |
| 4,502,159 A | 3/1985 | Woodroof et al. | |
| 4,539,716 A | 9/1985 | Bell | |
| 4,597,762 A | 7/1986 | Walter et al. | 623/1 |
| 4,629,458 A | 12/1986 | Pinchuk | |
| 4,703,108 A * | 10/1987 | Silver et al. | 530/356 |
| 4,787,900 A | 11/1988 | Yannas | 623/1 |
| 4,801,299 A | 1/1989 | Brendel | |
| 4,814,120 A | 3/1989 | Huc et al. | |
| 4,822,361 A | 4/1989 | Okita et al. | 623/12 |
| 4,842,575 A | 6/1989 | Hoffman, Jr. | |
| 4,863,666 A | 9/1989 | Primas et al. | |
| 4,863,668 A | 9/1989 | Griffiths et al. | |
| 4,889,120 A | 12/1989 | Gordon | |
| 4,902,289 A | 2/1990 | Yannas | 623/1 |
| 4,902,290 A | 2/1990 | Fleckenstein | |
| 4,902,508 A | 2/1990 | Badylak et al. | |
| 4,923,380 A | 5/1990 | Huc et al. | |
| 4,956,178 A | 9/1990 | Badylak et al. | 424/551 |
| 5,002,583 A | 3/1991 | Pitaru et al. | |
| 5,007,934 A | 4/1991 | Stone | |
| 5,024,671 A | 6/1991 | Tu et al. | |
| 5,026,381 A | 6/1991 | Li | |
| 5,028,695 A | 7/1991 | Eckmayer | |
| 5,037,377 A | 8/1991 | Alonso | |
| 5,061,276 A | 10/1991 | Tu et al. | 623/1 |
| 5,084,065 A | 1/1992 | Weldon et al. | |
| 5,106,949 A | 4/1992 | Kemp et al. | |
| 5,108,424 A | 4/1992 | Hoffman, Jr. et al. | |
| 5,131,908 A | 7/1992 | Dardik et al. | |
| 5,197,977 A | 3/1993 | Hoffman, Jr. et al. | |
| 5,219,576 A * | 6/1993 | Chu et al. | 424/484 |
| 5,256,418 A | 10/1993 | Kemp et al. | 424/423 |
| 5,263,983 A | 11/1993 | Yoshizato et al. | 623/12 |
| 5,263,984 A | 11/1993 | Li et al. | |

(Continued)

FOREIGN PATENT DOCUMENTS

CA 2183056 2/1995

(Continued)

OTHER PUBLICATIONS

Lawler et al., The Amer. J. of Surgery, vol. 12, Oct., pp. 517-519 (1971).

(Continued)

*Primary Examiner*—Bruce E. Snow
*Assistant Examiner*—Cheryl Miller
(74) *Attorney, Agent, or Firm*—Kramer Levin Naftalis & Frankel LLP

(57) ABSTRACT

A prosthesis, which, when implanted into a mammalian patient, serves as a functioning replacement for a body part, or tissue structure, and will undergo controlled biodegradation occurring concomitantly with bioremodeling by the patients living cells. The prosthesis is treated so that it is rendered non-antigenic so as not to elicit a significant humoral immune response. The prosthesis, in its various embodiments, thus has dual properties. First, it functions as a substitute body part, and second, it functions as bioremodeling template for the ingrowth of host cells.

25 Claims, No Drawings

U.S. PATENT DOCUMENTS

| | | | |
|---|---|---|---|
| 5,281,422 A | 1/1994 | Badylak | |
| 5,372,821 A | 12/1994 | Badylak | |
| 5,374,515 A | 12/1994 | Parenteau et al. | |
| 5,376,110 A | 12/1994 | Tu et al. | |
| 5,376,376 A | 12/1994 | Li | |
| 5,378,469 A | 1/1995 | Kemp et al. | 424/423 |
| 5,413,597 A | 5/1995 | Krajicek | |
| 5,445,833 A | 8/1995 | Badylak et al. | |
| 5,460,962 A | 10/1995 | Kemp | 435/238 |
| 5,480,424 A | 1/1996 | Cox | |
| 5,487,895 A * | 1/1996 | Dapper et al. | 424/278.1 |
| 5,523,291 A | 6/1996 | Janzen et al. | |
| 5,554,389 A | 9/1996 | Badylak et al. | |
| 5,567,806 A | 10/1996 | Abdul-Malak et al. | 530/356 |
| 5,571,216 A | 11/1996 | Anderson | 623/66 |
| 5,573,784 A | 11/1996 | Badylak et al. | |
| 5,645,860 A | 7/1997 | Knapp, Jr. et al. | |
| 5,693,085 A * | 12/1997 | Buirge et al. | 623/1.13 |
| 5,711,969 A | 1/1998 | Patel et al. | |
| 5,713,950 A | 2/1998 | Cox | |
| 5,733,337 A | 3/1998 | Carr, Jr. et al. | 623/11 |
| 5,755,791 A | 5/1998 | Whitson et al. | |
| 5,762,966 A | 6/1998 | Knapp, Jr. et al. | |
| 5,776,182 A | 7/1998 | Bruchman et al. | |
| 5,788,625 A | 8/1998 | Plouhar et al. | |
| 5,824,063 A | 10/1998 | Cox | |
| 5,851,230 A | 12/1998 | Weadock et al. | |
| 5,866,414 A * | 2/1999 | Badylak et al. | 435/325 |
| 5,879,383 A | 3/1999 | Bruchman et al. | |
| 5,885,619 A | 3/1999 | Patel et al. | |
| 5,893,888 A * | 4/1999 | Bell | 424/423 |
| 5,922,028 A | 7/1999 | Plouhar et al. | |
| 5,948,654 A | 9/1999 | Tranquillo et al. | |
| 5,955,110 A | 9/1999 | Patel et al. | |
| 5,968,092 A | 10/1999 | Buscemi et al. | |
| 5,968,096 A | 10/1999 | Whitson et al. | |
| 5,993,844 A | 11/1999 | Abraham et al. | |
| 5,997,575 A | 12/1999 | Whitson et al. | |
| 6,090,995 A * | 7/2000 | Reich et al. | 623/23.76 |
| 6,096,347 A | 8/2000 | Geddes et al. | |
| 6,099,567 A | 8/2000 | Badylak et al. | |
| 6,126,686 A | 10/2000 | Badylak et al. | |
| 6,176,880 B1 | 1/2001 | Plouhar et al. | |
| 6,187,039 B1 | 2/2001 | Hiles et al. | |
| 6,206,931 B1 | 3/2001 | Cook et al. | |
| 6,241,981 B1 | 6/2001 | Cobb et al. | |
| 6,334,872 B1 | 1/2002 | Termin et al. | |
| 6,572,650 B1 | 6/2003 | Abraham et al. | |

FOREIGN PATENT DOCUMENTS

| | | |
|---|---|---|
| EP | 397500 | 11/1990 |
| EP | 493788 | 7/1992 |
| EP | 564786 | 10/1993 |
| FR | 2679778 | 8/1991 |
| GB | 2153235 | 8/1985 |
| JP | 49-28193 | 7/1974 |
| JP | 59-177042 | 10/1984 |
| JP | 60-34450 | 2/1985 |
| JP | 1-230366 | 9/1989 |
| JP | 4-501516 | 3/1992 |
| JP | 5-344988 | 12/1993 |
| WO | WO 85/04413 | 10/1985 |
| WO | 89/10100 | 11/1989 |
| WO | WO 93/05798 | 4/1993 |
| WO | WO 93/10722 | 6/1993 |
| WO | 95/22301 | 8/1995 |
| WO | 95/28283 | 10/1995 |
| WO | 96/31157 | 10/1996 |
| WO | 98/06445 | 2/1998 |
| WO | 98/10775 | 3/1998 |
| WO | 98/25544 | 6/1998 |
| WO | 98/25545 | 6/1998 |
| WO | 98/25546 | 6/1998 |
| WO | 98/25637 | 6/1998 |
| WO | 98/25964 | 6/1998 |
| WO | 98/44969 | 10/1998 |
| WO | 99/12555 | 3/1999 |
| WO | 99/63051 | 12/1999 |
| WO | 00/32250 | 6/2000 |
| WO | 02/22184 | 3/2002 |

OTHER PUBLICATIONS

Dagan et al., Vascular Surgery, Jul./Aug., pp. 199-206 (1983).

Egusa S., Acta Md. Okayama vol. 22, pp. 153-165 (1968).

Fraser, et al. Arch. Surg. vol. 96, Mar., pp. 378-385 (1968).

Broll et al., Eus. Surg. Res. vol. 18, pp. 390-396 (1986).

Wyler et al., Journal of Biomedical Materials Research, vol. 26, pp. 1141-1146 (1992).

Hiles, M.C. et al., Journal of Biomedical Material Research, vol. 27, Feb. pp. 139-144 (1993).

Matsumoto, T. et al., Surgery, vol. 603, pp. 739-743 (1966).

Webster's II New Riverside University Dictionary, pp. 388, 1212, Copyright 1984, 1988, 1994 Houghton, Mifflin Company (1984).

Bronzino, J.D. (ed), The Biomechanical Engineering Handbook, CRC Press, Inc., Boca Raton, FL.

Chvapil, M. et al., Effect of Collagen Crosslinking on the Rate of Resorption of Implanted Collagen Tubing in Rabbits, (1977), J. Biomed. Matter Res. 11: 297-314.

Cooke, A. et al., An In Vitro Cytotoxicity Study of Aldehyde-Treated Pig Dermal Collagen, (1983), Br. J. Exp. Path 64: 172-176.

Kligman, A.M. et al., Histologic Response to Intradermal Zyderm and Zyplast (Glutaraldehyde Cross-Linked) Collagen in Humans, (1986), J. Dermatol. Surg. Oncol. 12(4): 351-357.

Harjula, A. et al., Histological Study of Glutaraldehyde-Processed Vascular Grafts of Biological Origin, (1980) ann. Chir. Gynaecol. 69: 256-262.

Roe, S.C. et al., Collagen Cross-Linking and Resorption: Effect of Glutaraldehyde Concentration, (1990), Artif. Organs 14: 443-448.

Rudolphy, VJ. et al., Chest Wall Reconstruction With Degradable Processed Sheep Dermal Collagen in Dogs, Ann Thorac Surg 52: 821-825, 1991.

Speer, D/P. et al., Biological Effects of Residual Glutaraldehyde in Glutaraldehyde-tanned Collagen Biomaterials, (1980) J. Biomed. Matter Res. 14: 753-764.

Viidik, A., Vuust, J. (eds), Biology of Collagen, Academic Press, London.

van Wachem, P.B., et al., In Vivo Degradation of Processed Dermal Sheep Collagen Evaluated with Transmission Electron Microscopy, Biomaterials 12(Mar.): 215-223, 1191.

Wiebe, D. et al., Glutaraldehyde Release from Vascular Prostheses of Biologic Origin, (1988) Surgery, 104: 26-33.

Woodroff, E.A., Use of Glutaraldehyde and Formaldehyde to Process Tissue Heart Valves, (1978),J. Bioeng. 2: 1-10.

Abbott, W.M. et al., Evaluation and Performance Standards for Arterial Prostheses, J. Vascular Surgery, 1993; 17:746-756.

Abraham, Ginger, Evaluation of the Porcine Intestinal Collagen Layer as a Biomaterial.

American National Standard for Vascular Graft Prostheses, by the Assoc. for the Advancement of Medical Instrumentation, approved Jul. 7, 1986.

Badylak, S., Endothelial Cell Adherence to Small Intestinal Submucosa: An Acellular Bioscaffold, Biomaterials 20, 2257-2263 (1999).

Bodnar, E., et al., Thorac. Cardiovascular Surg., 34:82-85 (1986).

Carr, R.M. et al., The Study of the Release of Benzalkonium-Heparin Complex from an Absorable Synthetic Colagen Graft, The 20th Annual Mtg of the Soc. for Biomaterials, 1994, Apr. 5-9, Boston, MA.

Courtman, et al., J. of Biomedical Research, 28:655-666 (1994).

Dejardin, L., Use of Small Intestinal Submucosal Implants for Regeneration of Large Fascial Defects: An experimental Study in Dogs.

Dobrin, Hypertension, 26: 38-43 (1995).

Gloeckner, D., Mechanical Evaluation and Design of a Multilayered Collagenous Repair Biomaterial.

Haimovici, Henry, Patch Graft Angioplasty, Vascular Surgery, Ed. pp. 287-292.

Kraiss et al., Circ. Res., 79: 45-53 (1996).

Mejita et al., Nature Medicine, 4: 235-39 (1998).

Onohara et al., J. Surg. Res., 55: 344-50 (1993).

Prevel, C., Small Intestinal Submucosa: Utilization as a Wound Dressing in Full-Thickness Rodent Wounds, Ann Plast Surg 35:381-388 (1995).

Prevel, C.D. Experimental Evaluation of Small Intestine Submucosa as a Microvascular Graft Material, Microsurgery 15:586-591 (1994).

Silverman, G.J., Sterilization and Preservation by Ionizing Irradiation, In Disinfection, Sterilization, and Preservation, Fourth Ed, London-Phil., Lea & Febiger, Ch. 32, 566-579.

Schwartz et al., J. Vasc. Surg. 15: 176-186 (1992).

Staros, Biochem., 21: 3950-55 (1982).

Takahashi and Berk, Journal of Clinical Investigation, 98: 2623-2631 (1996).

Termin, P.L. et al., Remodeling of an Absorbable Synthetic Collagen Graft: Long Term Implant Histology, 1994, the 20th Annual Mtg. of the Soc. for Biomaterials, Apr. 5-9, Boston, MA.

Wilson, G.J., et al., Ann. Thorac, Surg., 60:5353-5358 (1995).

Zwolak et al., J. Vasc. Surg., 5: 126-36 (1987).

* cited by examiner

TISSUE REPAIR FABRIC

BACKGROUND OF THE INVENTION

1. Field of the Invention

This invention is in the field of implantable biological prostheses. The present invention is a non-antigenic, resilient, completely bioremodelable, biocompatible tissue prosthesis which can be engineered into a variety of shapes and used to repair, augment, or replace mammalian tissues and organs. Each layer of the prosthesis is gradually degraded and remodeled by the host's cells which replace the implanted prosthesis in its entirety to restore structure and function and is useful for organ repair and reconstruction. Thus, the prosthesis acts as a template by which the host's cells will remodel themselves through a process that will replace the prosthetic collagen molecules with the appropriate host cells in order to restore and replace the original host tissue or organ.

2. Brief Description of the Background of the Invention

Despite the growing sophistication of medical technology, repairing and replacing damaged tissues remains a frequent, costly, and serious problem in health care. Currently implantable prostheses are made from a number of synthetic and treated natural materials. The ideal prosthetic material should be chemically inert, non-carcinogenic, capable of resisting mechanical stress, capable of being fabricated in the form required, and sterilizable, yet not be physically modified by tissue fluids, excite an inflammatory or foreign body reaction, induce a state of allergy or hypersensitivity, or, in some cases, promote visceral adhesions (Jenkins S. D., et al. *Surgery* 94(2):392–398, 1983).

For example, body wall defects that cannot be closed with autogenous tissue due to trauma, necrosis or other causes require repair, augmentation, or replacement with synthetic mesh. In reinforcing or repairing abdominal wall defects, several prosthetic materials have been used, including tantalum gauze, stainless steel mesh, DACRON®, ORLON®, FORTISAN®, nylon, knitted polypropylene (MARLEX®), microporous expanded-polytetrafluoroethylene (GORE-TEX®), dacron reinforced silicone rubber (SILASTIC®), polyglactin 910 (VICRYL®), polyester (MERSWENE®), polyglycolic acid (DEXON®), processed sheep dermal collagen (PSDC®), crosslinked bovine pericardium (PERIGUARD®), and preserved human dura (LYODURA®). No single prosthetic material has gained universal acceptance.

The major advantages of metallic meshes are that they are inert, resistant to infection and can stimulate fibroplasia. Their major disadvantage is the fragmentation that occurs after the first year of implantation as well as the lack of malleability. Synthetic meshes have the advantage of being easily molded and, except for nylon, retain their tensile strength in the body. European Patent No. 91122196.8 to Krajicek details a triple-layer vascular prosthesis which utilizes non-resorbable, synthetic mesh as the center layer. The synthetic textile mesh layer is used as a central frame to which layers of collagenous fibers can be added, resulting in the tri-layered prosthetic device. The major disadvantage of a non-resorbable synthetic mesh is lack of inertness, susceptibility to infection, and interference with wound healing.

In contrast to the non-resorbable mesh disclosed in Krajicek (E.P. No. 91122196.8), absorbable synthetic meshes have the advantage of impermanence at the site of implantation, but often have the disadvantage of losing their mechanical strength, because of dissolution by the host, prior to adequate cell and tissue ingrowth.

The most widely used material for abdominal wall replacement and for reinforcement during hernia repairs is MARLEX®; however, several investigators reported that with scar contracture, polypropylene mesh grafts became distorted and separated from surrounding normal tissue in a whorl of fibrous tissue. Others have reported moderate to severe adhesions when using MARLEX®.

GORE-TEX® is currently believed to be the most chemically inert polymer and has been found to cause minimal foreign body reaction when implanted. A major problem exists with the use of polytetrafluoroethylene in a contaminated wound as it does not allow for any macromolecular drainage, which limits treatment of infections.

Collagen first gained utility as a material for medical use because it was a natural biological prosthetic substitute that was in abundant supply from various animal sources. The design objectives for the original collagen prosthetics were the same as for synthetic polymer prostheses; the prosthesis should persist and essentially act as an inert-material. With these objectives in mind, purification and crosslinking methods were developed to enhance mechanical strength and decrease the degradation rate of the collagen (Chvapil, M., et al (1977) *J. Biomed. Mater. Res*. 11: 297–314; Kligman, A. M., et al (1986) *J. Dermatol. Surg. Oncol*. 12 (4): 351–357; Roe, S. C., et al. (1990). *Artif. Organs*. 14: 443–448. Woodroff, E. A. (1978). *J. Bioeng*. 2: 1–10). Crosslinking agents originally used include glutaraldehyde, formaldehyde, polyepoxides, diisocyanates (Borick P. M., et al. (1964) *J. Pharm. Sci*. 52: 1273–1275), and acyl azides. Processed dermal sheep collagen has been studied as an implant for a variety of applications. Before implantation, the sheep dermal collagen is typically tanned with hexamethylenediisocyanate (van Wachem, P. B., et al. *Biomaterials* 12(March):215–223, 1991) or glutaraldehyde (Rudolphy, V. J., et al. *Ann Thorac Surg* 52:821–825, 1991). Glutaraldehyde, probably the most widely used and studied crosslinking agent, was also used as a sterilizing agent. In general, these crosslinking agents generated collagenous material which resembled a synthetic material more than a natural biological tissue, both mechanically and biologically.

Crosslinking native collagen reduces the antigenicity of the material (Chvapil, M. (1980) Reconstituted collagen. pp. 313–324. In: Viidik, A., Vuust, J. (eds), *Biology of Collagen*. Academic Press, London; Harjula, A., et al. (1980) *Ann. Chir. Gynaecol*. 69: 256–262.) by linking the antigenic epitopes rendering them either inaccessible to phagocytosis or unrecognizable by the immune system. There are many known methods of crosslinking collagenous materials. U.S. Pat. No. 5,571,216 details several methods of achieving crosslinking through the heating and joining of free ends of collagen tendrils. U.S. Pat. No. 5,263,983 to Yoshizato details crosslinking by treating collagenous composites with 1-ethyl-3-(3-dimethylaminopropyl) carbodiimide hydrochloride. Glutaraldehyde is also employed as a reagent in crosslinking (See U.S. Pat. No. 4,787,900 to Yannas; U.S. Pat. No. 4,597,762 to Walter). However, data from studies using glutaraldehyde as the crosslinking agent are hard to interpret since glutaraldehyde treatment is also known to leave behind cytotoxic residues (Chvapil, M. (1980), supra; Cooke, A., et al. (1983) *Br. J. Exp. Path*. 64: 172–176; Speer, D. P., et al. (1980) *J. Biomed. Mater. Res*. 14: 753–764; Wiebe, D., et al. (1988) *Surgery*. 104: 26–33). It is, therefore, possible that the reduced antigenicity associated with glutaraldehyde crosslinking is due to non-specific cytotoxicity rather than a specific effect on antigenic determinants. Glutaraldehyde treatment is an acceptable way to increase durability and reduce antigenicity of collagenous materials as compared to those that are noncrosslinked. However, glutaraldehyde crosslinking collagen materials significantly limits the body's ability to remodel the prosthesis (Roe, S. C., et al. (1990), supra).

All of the above problems associated with traditional materials stem, in part, from the inability of the body to recognize any implant as "inert". Although biologic in origin, extensive chemical modification of collagen tends to render it as "foreign". To improve the long term performance of implanted collagenous devices, it is important to retain many of the properties of the natural collagenous tissue. In this "tissue engineering"0 approach, the prosthesis is designed not as a permanent implant but as a scaffold or template for regeneration or remodeling. Tissue engineering design principles incorporate a requirement for isomorphous tissue replacement, wherein the biodegradation of the implant matrix occurs at about the same functional rate of tissue replacement (Yannas, I. V. (1995) Regeneration Templates. pp. 1619–1635. In: Bronzino, J. D. (ed.), The Biomedical Engineering Handbook, CRC Press, Inc., Boca Raton, Fla.).

When such a prosthesis is implanted, it should immediately serve its requisite mechanical and/or biological function as a body part. The prosthesis should also support appropriate host cellularization by ingrowth of mesenchymal cells, and in time, through isomorphous tissue replacement, be replaced with host tissue, wherein the host tissue is a functional analog of the original tissue. In order to do this, the implant must not elicit a significant humoral immune response or be either cytotoxic or pyrogenic to promote healing and development of the neo-tissue.

Prostheses or prosthetic material derived from isolated collagen molecules, either in powder form or in a solution, have been investigated for surgical repair or for tissue and organ replacement. The source of collagen used in these prosthetic devices is determinate of the prostheses' form and function. U.S. Pat. No. 4,787,900 to Yannas details a process for the creation of prosthetic blood vessels out of a collagenous composite formed, ex vivo, from individual collagen molecules in either powder or solution form. The collagenous compound is a conglomerate of individual collagen molecules and does not retain any of the structural characteristics of the tissue from which the collagen was originally derived. Instead, this collagenous composite is a "tangled mass of collagen fibrils" that is later chemically tailored into the desired shape and thickness required for repairing the specific blood vessel.

Prostheses or prosthetic material derived from explanted mammalian tissue have been widely investigated for surgical repair or for tissue and organ replacement. The tissue is typically processed to remove cellular components leaving a natural tissue matrix. Further processing, such as crosslinking, disinfecting or forming into shapes have also been investigated. U.S. Pat. No. 3,562,820 to Braun discloses tubular, sheet and strip forms of prostheses formed from submucosa adhered together by use of a binder paste such as a collagen fiber paste or by use of an acid or alkaline medium. U.S. Pat. No. 4,502,159 to Woodroof provides a tubular prosthesis formed from pericardial tissue in which the tissue is cleaned of fat, fibers and extraneous debris and then placed in phosphate buffered saline. The pericardial tissue is then placed on a mandrel and the seam is then closed by suture and the tissue is then crosslinked. U.S. Pat. No. 4,703,108 to Silver provides a biodegradable matrix from soluble collagen solutions or insoluble collagen dispersions which are freeze dried and then crosslinked to form a porous collagen matrix. U.S. Pat. No. 4,776,853 to Kle- ment provides a process for preparing biological material for implant that includes extracting cells using a hypertonic solution at an alkaline pH followed by a high salt solution containing detergent; subjecting the tissue to protease free enzyme solution and then an anionic detergent solution. U.S. Pat. No. 4,801,299 to Brendel discloses a method of processing body derived whole structures for implantation by treating the body derived tissue with detergents to remove cellular structures, nucleic acids, and lipids, to leave an extracellular matrix which is then sterilized before implantation. U.S. Pat. No. 4,902,508 to Badylak discloses a three layer tissue graft composition derived from small intestine comprising tunica submucosa, the muscularis mucosa, and stratum compactum of the tunica mucosa. The method of obtaining tissue graft composition comprises abrading the intestinal tissue followed by treatment with an antibiotic solution. U.S. Pat. No. 5,336,616 to Livesey discloses a method of processing biological tissues by treatment of tissue to remove cells, treatment with a cryoprotectant solution, freezing, rehydration, and finally, innoculation with cells to repopulate the tissue. U.S. Pat. No. 4,597,762 to Walter discloses a method of preparing collagenous prostheses through proteolysis, crosslinking with glutaraldehyde, welding and subsequent sterilization of animal hide or other mammalian tissues.

It is a continuing goal of researchers to develop implantable prostheses which can successfuily be used to replace or to facilitate the repair of mammalian tissues, such as abdominal wall defects and vasculature, so that the intrinsic strength, resilience, and biocompatability of the host's own cells may be optimally exploited in the repair process.

SUMMARY OF THE INVENTION

The present invention overcomes the difficulties of the materials currently available and provides a prosthetic device for use in the repair, augmentation, or replacement of damaged tissues and organs. This invention is directed to a prosthetic material, which, when implanted into a mammalian host, undergoes controlled biodegradation accompanied by adequate living cell replacement, or neo-tissue formation, such that the original implanted prosthesis is ultimately remodeled and completely replaced by host derived tissue and cells. The prosthesis of this invention, a material for tissue repair, comprises a non-antigenic, sterile, completely bioremodelable collagenous material derived from manunalian tissue. The prosthesis of this invention utilizes preexisting, naturally-formed layers of biological collagen for surgical repair or for tissue and organ replacement. Unlike the tissue repair fabrics that are currently available, which use collagenous composites formed from reconstituted individual collagen molecules, the collagenous tissue of the present invention retains the structural characteristics of the tissue from which it has been derived. This collagenous tissue of the present invention is able to be layered and bonded together to form multilayer sheets, tubes, or complex shaped prostheses. The bonded collagen layers of the invention are structurally stable, pliable, semi-permeable, and suturable.

Each layer of the prosthetic material of this invention are completely bioremodelable and is replaced by host cells to effectively become a host tissue. Moreover, because the present invention is comprised of naturally-formed preexisting collagen layers which have been harvested from other mammillian tissues, the risk of a significant humoral response has been greatly decreased. It is, therefore, an object of this invention to provide a tissue repair fabric that does not exhibit the above-mentioned shortcomings associated with many of the grafts now being used clinically.

Another object is the provision of a prosthetic material that will allow for and facilitate tissue ingrowth and/or organ regeneration at the site of implantation that is a sterile, non-pyrogenic, and non-antigenic material derived from mammalian collagenous tissue. Prostheses prepared from this material, when engrafted to a recipient host or patient, do not elicit a significant humoral immune response. Instead, the prostheses is accepted into the recipient host or patient as non-foreign material and the bioremodeling can proceed without interference from potential immune responses to foreign materials. Prostheses formed from the material concomitantly undergoes controlled bioremodeling occurring with adequate living cell replacement such that the original implanted prosthesis is completely remodeled by the patient's living cells to form a regenerated organ or tissue.

A further object of the current invention is to provide a simple, repeatable method for manufacturing a tissue repair fabric.

Still another object of this invention is to provide a method for use of a novel multipurpose tissue repair fabric in autografting, allografting, and heterografting indications.

Still a further object is to provide a novel tissue repair fabric that can be implanted using conventional surgical techniques.

DETAILED DESCRIPTION OF THE INVENTION

This invention is directed to tissue engineered prostheses, which, when implanted into a mammalian host, can serve as a functioning repair, augmentation, or replacement body part, or tissue structure, and will undergo controlled biodegradation occurring concomitantly with remodeling by the host's cells. The prosthesis of this invention, in its various embodiments, thus has dual properties: First, it functions as a substitute body part, and second, while still functioning as a substitute body part, it functions as a remodeling template for the ingrowth of host cells. In order to do this, the prosthetic material of this invention, a tissue repair fabric, was developed comprising mammalian derived collagenous tissue that is rendered non-antigenic and is able to be bonded to itself or another. Although the prostheses will be illustrated through construction of various devices and constructs, the invention is not so limited. It will be appreciated that the device design in its shape and thickness is to be selected depending on the ultimate indication for the construct.

In the preferred embodiment, the collagenous material from which to form prostheses, or the prosthesis itself, is rendered sterile, non-pyrogenic, and non-antigenic. The prosthesis, when engrafted to a recipient host or patient, does not elicit a significant humoral immune response. An acceptable level of response is one that demonstrates no significant increase in antibody titer to collagenous tissue proteins from baseline titer levels when blood serum obtained from a recipient of a prosthesis is tested for antibodies to proteins in extracts of the collagenous tissue.

In the preferred method, the tissue repair material or the prosthesis itself is rendered non-antigenic, while maintaining the ability for the prosthesis to concomitantly undergo controlled bioremodeling occurring with adequate living cell replacement. The method of preparing a non-antigenic prosthetic collagen material, comprises disinfection of the material by a method to prevent microbial degradation of the material, preferably by use of a solution comprising peracetic acid; and crosslinking the disinfected collagen material with a crosslinking agent, preferably 1-ethyl-3-(3-dimethylaminopropyl) carbodiimide hydrochloride (EDC).

Also in the preferred embodiment, collagenous tissues derived from the mammalian body are used to make said collagen material. Collagenous tissue sources include, but are not limited to intestine, fascia lata, pericardium, and dura mater. The most preferred material for use is the tunica submucosa layer of the small intestine. The tunica submucosa is preferably separated, or delaminated, from the other layers of the small intestine. This layer is referred to hereinafter as the Intestinal Collagen Layer ("ICL"). Further, the collagen layers of the prosthetic device may be from the same collagen material, such as two or more layers of ICL, or from different collagen materials, such as one or more layers of ICL and one or more layers of facia lata.

The submucosa, or the intestinal collagen layer (ICL), from a mammalian source, typically pigs, cows, or sheep, is mechanically cleaned by squeezing the raw material between opposing rollers to remove the muscular layers (tunica muscularis) and the mucosa (tunica mucosa). The tunica submucosa of the small intestine is harder and stiffer than the surrounding tissue, and the rollers squeeze the softer components from the submucosa. In the examples that follow, the ICL was mechanically harvested from porcine small intestine using a Bitterling gut cleaning machine.

As the mechanically cleaned submucosa may have some hidden, visibly nonapparent debris that affects the consistency of the mechanical properties, the submucosa may be chemically cleaned to remove debris and other substances, other than collagen, for example, by soaking in buffer solutions at 4° C., or by soaking with NaOH or trypsin, or other known cleaning techniques. Alternative means employing detergents such as TRITON X-100™ (Rohm and Haas) or sodium dodecylsulfate (SDS); enzymes such as dispase, trypsin, or thermolysin; and/or chelating agents such as ethylenediaminetetracetic acid (EDTA) or ethylenebis(oxyethylenitrilo)tetracetic acid (EGTA) may also be included in the chemical cleaning method.

After cleaning, the (ICL) should be decontaminated or disinfected, preferably with the use of dilute peracetic acid solutions as described in U.S. Pat. No. 5,460,962, incorporated herein by reference. Decontamination or disinfection of the material is done to prevent degradation of the collagenous matrix by bacteria or proteolytic enzymes. Other disinfectant solutions and systems for use with collagen are known in the art and can be used so long as after the disinfection treatment there is no interference in the ability of the material to be remodeled.

In a preferred embodiment, the prosthetic device of this invention has two or more superimposed collagen layers that are bonded together. As used herein, "bonded collagen layers" means composed of two or more layers of the same or different collagen material treated in a manner such that the layers are superimposed on each other and are sufficiently held together by self-lamination. The bonding of the collagen layers may be accomplished in a number of different ways: by heat welding or bonding, adhesives, chemical linking, or sutures.

In the preferred method, and in the examples that follow, the ICL is disinfected with a peracetic acid solution at a concentration between about 0.01 and 0.3% v/v in water, preferably about 0.1%, at a neutralized pH between about pH 6 and pH 8 and stored until use at about 4° C. in phosphate buffered saline (PBS). The ICL is cut longitudinally and flattened onto a solid, flat plate. One or more successive layers are then superimposed onto one another. A second solid flat plate is placed on top of the layers and the two plates are clamped tightly together. The complete apparatus, clamped plates and collagen layers, are then heated for a time and under conditions sufficient to effect the bonding of the collagen layers together. The amount of heat applied should be sufficiently high to allow the collagen to bond, but not so high as to cause the collagen to irreversibly denature. The time of the heating and bonding will depend upon the type of collagen material layer used, the moisture content and thickness of the material, and the applied heat. A typical range of heat is from about 50° C. to about 75° C., more typically 60° C. to 65° C. and most typically 62° C. A typical range of times will be from about 7 minutes to about 24 hours, typically about one hour. The degree of heat and the amount of time that the heat is applied can be readily ascertained through routine experimentation by varying the heat and time parameters. The bonding step may be accomplished in a conventional oven, although other apparatus or heat applications may be used including, but not limited to, a water bath, laser energy, or electrical heat conduction. Immediately following the heating and bonding, the apparatus is cooled, in air or a water bath, at a range between room temperature at 20° C. and 1° C. Rapid cooling, termed quenching, will immediately, or almost immediately, stop the heating action. To accomplish this step, the apparatus may be cooled, typically in a water bath, with a temperature preferably between about 1° C. to about 10° C., most preferably about 4° C. Although cooling temperatures below 1° C. may be used, care will need to be taken not to freeze the collagen layers, which may cause structural damage. In addition, temperatures above 10° C. may be used in quenching, but if the temperature of the quench is too high, then the heating may not be stopped in time to sufficiently fix the collagen layers in their current configuration.

The prosthetic material or multi-layered construct is preferably then crosslinked. Crosslinking the bonded prosthetic device provides strength and some durability to the device to improve handling properties. Crosslinking agents should be selected so as to produce a biocompatible material capable of being remodeled by host cells. Various types of crosslinking agents are known in the art and can be used such as ribose and other sugars, oxidative agents and dehydrothermal (DHT) methods. A preferred crosslinking agent is 1-ethyl-3-(3-dimethylaminopropyl) carbodiimide hydrochloride (EDC). The crosslinking solution containing EDC and water may also contain acetone. In a preferred embodiment, sulfo-N-hydroxysuccinimide is added to the crosslinking agent (Staros, J. V., *Biochem.* 21, 3950–3955, 1982).

In a preferred embodiment, a method comprising disinfection with peracetic acid and subsequent crosslinking with EDC of the ICL material is performed to reduce the antigenicity of the material. The immunoreactive proteins present in non-sterilized, non-crosslinked ICL are either reduced or removed, or their epitopes have been modified such that they no longer elicit a significant humoral immune response. Graft implants of this material do, however, show an initial transient inflammatory response as a result of a wound healing response. As used herein, the term "non-antigenic" means not eliciting a significant humoral immune response in a host or patient in whom a prosthesis is implanted. An acceptable level of response is one that demonstrates no significant increase in antibody titer to collagenous tissue proteins from baseline titer levels when blood serum obtained from a recipient of a prosthesis is tested for antibodies to proteins in extracts of the collagenous tissue. For a patient or host previously non-sensitized to collagenous tissue proteins, the preferable serum antibody titer is 1:40 or less.

Prostheses of the preferred embodiment are also preferably non-pyrogenic. A prosthesis that is pyrogenic, when engrafted to a recipient host or patient, will cause a febrile reaction in the patient, thus affecting the ability of the prosthesis to be remodeled. Pyrogens are tested by intravenous injection of a solution containing a sample of material into three test rabbits. A temperature sensing probe is positioned in the rectum of the rabbits to monitor temperature changes. If there is a rise in temperature in any rabbit above 0.5° C., then the test for that sample is continued in five more rabbits. If not more than three of the eight rabbits show individual rises in temperature of 0.5° C. or more and the sum of the eight individual maximum temperature rises does not exceed 3.3° C., the material under examination meets the requirements for the absence of pyrogens. (Pyrogen Test (151), pp. 1718–1719. In: *The United States Pharmacopeia (USP)* 23 The United States Pharmacopeial Convention, Inc., Rockville, Md.)

The tissue repair fabric of this invention, functioning as a substitute body part, may be flat, tubular, or of complex geometry. The shape of the tissue repair fabric will be decided by its intended use. Thus, when forming the bonding layers of the prosthesis of this invention, the mold or plate can be fashioned to accommodate the desired shape. The tissue repair fabric can be implanted to repair, augment, or replace diseased or damaged organs, such as abdominal wall defects, pericardium, hernias, and various other organs and structures including, but not limited to, bone, periosteum, perichondrium, intervertebral disc, articular cartilage, dermis, epidermis, bowel, ligaments, and tendons. In addition, the tissue repair fabric can be used as a vascular or intracardiac patch, or as a replacement heart valve.

Flat sheets may be used, for example, to support prolapsed or hypermobile organs by using the sheet as a sling for the organs. This sling can support organs such as bladder or uterus.

Tubular grafts may be used, for example, to replace cross sections of tubular organs such as vasculature, esophagus, trachea, intestine, and fallopian tubes. These organs have a basic tubular shape with an outer surface and a lurinal surface.

In addition, flat sheets and tubular structures can be formed together to form a complex structure to replace or augment cardiac or venous valves.

In addition to functioning as a substitute body part or support, the second function of the prosthesis is that of a template or scaffold for bioremodeling. "Bioremodeling" is used herein to mean the production of structural collagen, vascularization, and epithelialization by the ingrowth of host cells at a functional rate about equal to the rate of biodegradation of the implanted prosthesis by host cells and enzymes. The tissue repair fabric retains the characteristics of the originally implanted prosthesis while it is remodeled by the host into all, or substantially all, host tissue, and as such, is functional as an analog of the tissue it repairs or replaces. Thus, each layer of the prosthesis is completely bioremodelable and subsequently replaced by host cells.

The mechanical properties include mechanical integrity such that the tissue repair fabric resists creep during bioremodeling, and additionally is pliable and suturable. The term "pliable" means good handling properties. The term "suturable" means that the mechanical properties of the layer include suture retention which permits needles and suture materials to pass through the prosthesis material at the time of suturing of the prosthesis to sections of native tissue, a process known as anastomosis. During suturing, such prostheses must not tear as a result of the tensile forces applied to them by the suture, nor should they tear when the suture is knotted. Suturability of tissue repair fabric, i.e., the ability of prostheses to resist tearing while being sutured, is related to the intrinsic mechanical strength of the prosthesis material, the thickness of the graft, the tension applied to the suture, and the rate at which the knot is pulled closed.

As used herein, the term "non-creeping" means that the biomechanical properties of the prosthesis impart durability so that the prosthesis is not stretched, distended, or expanded beyond normal limits after implantation. As is described below, total stretch of the implanted prosthesis of this invention is within acceptable limits. The prosthesis of this invention acquires a resistance to stretching as a function of post-implantation cellular bioremodeling by replacement of structural collagen by host cells at a faster rate than the loss of mechanical strength of the implanted materials due from biodegradation and remodeling. The tissue repair fabric of the present invention is "semi-permeable," even though it has been crosslinked. Semi-permeability permits the ingrowth of host cells for remodeling or for deposition of the collagenous layer. The "non-porous" quality of the prosthesis prevents the passage of fluids that are intended to be retained by the implantation of the prosthesis. Conversely, pores may be formed in the prosthesis if the quality is required for an application of the prosthesis.

The mechanical integrity of the prosthesis of this invention is also in its ability to be draped or folded, as well as the ability to cut or trim the prosthesis obtaining a clean edge without delaminating or fraying the edges of the construct.

Additionally, in another embodiment of the invention, mechanically sheared or chopped collagen fibers can be included between the collagen layers adding bulk to the construct and providing a mechanism for a differential rate of remodeling by host cells. The properties of the construct incorporating the fibers may be altered by variations in the length and diameter of the fibers; variations on the proportion of the fibers used, and fully or partially crosslinking fibers. The length of the fibers can range from 0.1 cm to 5.0 cm.

In another embodiment of the invention, collagen threads, such as those disclosed in U.S. Pat. No. 5,378,469 and incorporated herein by reference, can be incorporated into the multilayered tissue repair fabric for reinforcement or for different functional rates of remodeling. For example, a helix or "twist", of a braid of 20 to 200 denier collagen thread may be applied to the surface of the tissue repair fabric. The diameter size of the helix or braid of collagen thread can range from 50 to 500 microns, preferably 100 to 200 microns. Thus, the properties of the tissue repair fabric layer can be varied by the geometry of the thread used for the reinforcement. The functionality of the design will be dependent on the geometry of the braid or twist. Additionally, collagen thread constructs such as a felt, a flat knitted or woven fabric, or a three-dimensional knitted, woven or braided fabric may be incorporated between the layers or on the surface of the construct. Some embodiments may also include a collagen gel between the layers alone or with a drug, growth factor or antibiotic to function as a delivery system. Additionally, a collagen gel could be incorporated with a thread or a thread construct between the layers.

As will be appreciated by those of skill in the art, many of the embodiments incorporating collagen gel, thread or a thread construct will also affect the physical properties, such as compliance, radial strength, kink resistance, suture retention, and pliability. Physical properties of the thread or the thread construct may also be varied by crosslinking the threads.

In some embodiments, additional collagenous layers may be added to the outer or inner surfaces of the bonded collagen layers to create a smooth flow surface for its ultimate application as described in PCT International Publication No. WO 95/22301, the contents of which are incorporated herein by reference. This smooth collagenous layer also promotes host cell attachment which facilitates ingrowth and bioremodeling. As described in PCT International Publication No. WO 95/22301, this smooth collagenous layer may be made from acid-extracted fibrillar or non-fibrillar collagen, which is predominantly type I collagen, but may also include other types of collagen. The collagen used may be derived from any number of mammalian sources, typically bovine, porcine, or ovine skin or tendons. The collagen preferably has been processed by acid extraction to result in a fibril dispersion or gel of high purity. Collagen may be acid-extracted from the collagen source using a weak acid, such as acetic, citric, or formic acid. Once extracted into solution, the collagen can be salt-precipitated using NaCl and recovered, using standard techniques such as centrifugation or filtration. Details of acid extracted collagen from bovine tendon are described, for example, in U.S. Pat. No. 5,106,949, incorporated herein by reference.

Collagen dispersions or gels for use in the present invention are generally at a concentration of about 1 to 10 mg/mL, preferably, from about 2 to 6 mg/mL, and most preferably at about 3 to 5 mg/mL and at pH of about 2 to 4. A preferred solvent for the collagen is dilute acetic acid, e.g., about 0.05 to 0.1%. Other conventional solvents for collagen may be used as long as such solvents are compatible.

Once the prosthetic device has been produced, it may be air dried, packaged, and sterilized with gamma irradiation, typically 2.5 Mrad, and stored. Terminal sterilization employing chemical solutions such as peracetic acid solutions as described in U.S. Pat. No. 5,460,962, incorporated herein, may also be used.

In the examples that follow; the ICL is cut longitudinally and flattened out onto a glass plate, although any inert non-insulated firm mold may be used. In addition, the mold can be any shape: flat, rounded, or complex. In a rounded or complex mold, the bottom and upper mold pieces will be appropriately constructed so as to form the completed prosthesis into the desired shape. Once so constructed, the prosthesis will keep its shape. Thus, for example, if the prosthesis is formed into a rounded shape, it can be used as a heart valve leaflet replacement.

The multi-layered tissue repair fabric may be tubulated by various alternative means or combinations thereof. The multilayered tissue repair fabric may be formed into a tube in either the normal or the everted position. The tube may be made mechanically by suturing, using interrupted sutures with suitable suture material and is advantageous as it allows the tube to be trimmed and shaped by the surgeon at the time of implantation without unraveling. Other processes to seam the submucosa may include adhesive bonding, such as the use of fibrin-based glues or industrial-type adhesives such as polyurethane, vinyl acetate or polyepoxy. Preferably heat bonding techniques may also be used including laser welding or heat welding of the seam, followed by quenching, to seal the sides of the thus formed tube. Other mechanical means are possible, such as using pop rivets or staples. With these tubulation techniques, the ends of the sides may be either butt ended or overlapped. If the sides are overlapped, the seam may be trimmed once the tube is formed. In addition, these tubulation techniques are typically done on a mandrel so as to determine the desired diameter.

The thus formed structural tube can be kept on a mandrel or other suitable spindle for further processing. To control functional rates of biodegradation and therefore the rate of prosthesis strength decrease during bioremodeling, the prosthesis is preferably crosslinked, using a suitable * crosslinking agent, such as 1-ethyl-3-(3-dimethylaminopropyl) carbodiumide hydrochloride (EDC). Crosslinking the prosthesis also aids in preventing luminal creep, in keeping the tube diameter uniform, and in increasing the burst strength. The bond strength of a seam or multilayer prosthesis is increased when heat or dehydration bonding methods are used. It is believed that crosslinking the intestinal collagen layer also improves the suture retention strength by improving resistance to crack propagation.

Collagen may be deposited on the internal or external surface of the ICL as described in Example 5 of U.S. Pat. No. 5,256,418, incorporated herein by reference. Briefly, when the tissue repair fabric is to be tubulated, the multi-layered fabric is fitted at one end by luer fittings and the collagen dispersion fills the tube. This step may also be accomplished as described in the above-referenced patent application using a hydrostatic pressure head. The inner layer of collagen can also be deposited by flowing collagen into both ends of the tube simultaneously. The tube is then placed into a bath of 20% polyethylene glycol (PEG) in isotonic phosphate buffered saline (PBS), neutral pH. The osmotic gradient between the internal collagen solution and outer PEG solution in combination cause a simultaneous concentration and deposition of the collagen along the lumen of the internal structural layer wall. The tube is then removed from the PEG bath, and a glass rod with a desired diameter of the prosthesis lumen is inserted into the collagen solution, or alternatively, one end of the prosthesis is closed and air pressure is applied internally to keep the tube lumen open. The prosthesis is then allowed to dry and subsequently is rehydrated in PBS. The thus formed collagen coating, in the form of a dense fibrillar collagen, fills slight irregularities in the intestinal structural layer, thus resulting in a prosthesis with both a smooth flow surface and a uniform thickness. The procedure also facilitates the bonding of the collagen gel to the intestinal collagen layer. A collagenous layer of varying thickness and density can be produced by changing the deposition conditions which can be determined by routine parameter changes. The same procedures can be used to apply the collagen to the outer surface of the ICL to create a three-layer prosthesis.

The prosthesis construct is thrombogenic in small diameter blood vessel replacements. It can only be used in vascular applications in high flow (large diameter) vessels. Therefore, the prosthesis must be rendered non-thrombogenic if to be useful for small diameter blood vessel repair or replacement.

Heparin can be applied to the prosthesis, by a variety of well-known techniques. For illustration, heparin can be applied to the prosthesis in the following three ways. First, benzalkonium heparin (BA-Hep) solution can be applied to the prosthesis by dipping the prosthesis in the solution and then air-drying it. This procedure treats the collagen with an ionically bound BA-Hep complex. Second, EDC can be used to activate the heparin, then to covalently bond the heparin to the collagen fiber. Third, EDC can be used to activate the collagen, then covalently bond protamine to the collagen and then ionically bond heparin to the protamine. Many other coating, bonding, and attachment procedures are well known in the art which could also be used.

Treatment of the tissue repair fabric with drugs in addition to or in substitution for heparin may be accomplished. The drugs may include for example, growth factors to promote vascularization and epithelialization, such as macrophage derived growth factor (MDGF), platelet derived growth factor (PDGF), endothelial cell derived growth factor (ECDGF); antibiotics to fight any potential infection from the surgery implant; or nerve growth factors incorporated into the inner collagenous layer when the prosthesis is used as a conduit for nerve regeneration. In addition to or in substitution for drugs, matrix components such as proteoglycans or glycoproteins or glycosaminoglycans may be included within the construct.

The tissue repair fabric can be laser drilled to create micron sized pores, through the completed prosthesis for aid in cell ingrowth using an excimer laser (e.g. at KrF or ArF wavelengths). The pore size can vary from 10 to 500 microns, but is preferably from about 15 to 50 microns and spacing can vary, but about 500 microns on center is preferred. The tissue repair fabric can be laser drilled at any time during the process to make the prosthesis, but is preferably done before decontamination or sterilization.

Voids or spaces can also be formed by the method of phase inversion. At the time of layering the ICL, between layers is distributed crystalline particles that are insoluble in the liquid heat source for bonding but should be soluble in the quench bath or the crosslinking solution. If laser or dry heat is used to bond the layers then any soluble crystalline solid may be used as long as it is soluble in the quench bath or the crosslinking solution. When the crystalline solid is solubilized and has diffused out, there remains a space in-which the solid had occupied. The size of the particles may vary from 10 to 100 microns, but is preferably from about 15 to 50 microns and spacing can vary between particles when distributed between the layers. The number and size of the voids formed will also affect the physical properties (i.e., compliance, kink resistance, suture retention, pliability).

The following examples are provided to better elucidate the practice of the present invention and should not be interpreted in any way to limit the scope of the present invention. Those skilled in the art will recognize that various modifications, can be made to the methods described herein while not departing from the spirit and scope of the present invention.

EXAMPLES

Example 1

Harvesting and Processing of the Intestinal Collagen Layer from Porcine Intestine The small intestine of a pig was harvested and mechanically stripped, using a Bitterling gut cleaning machine (Nottingham, UK) which forcibly removes the fat, muscle and mucosal layers from the tunica submucosa using a combination of mechanical action and washing using hot water. The mechanical action can be described as a series of rollers that compress and strip away the successive layers from the tunica submucosa when the intact intestine is run between them. The tunica submucosa of the small intestine is harder and stiffer than the surrounding tissue, and the rollers squeeze the softer components from the submucosa. The result of the machine cleaning was such that the submucosal layer of the intestine solely remained. Finally, the submucosa was decontaminated with 0.3% peracetic acid for 18 hours at 4° C. and then washed in phosphate buffered saline. The product that remained was an intestinal collagen layer (ICL).

Example 2

Various Welding Temperatures and EDC Concentrations of ICL

The effects of welding temperature (followed by quenching), weld time, 1-ethyl-3-(3-(dimethylamino)propyl)carbodiimide (EDC) concentration, acetone concentration and crosslinking time, after welding on weld strength were examined for the ICL two layered tube application. ICL was porcine derived as described in the Example 1. Strength qualities were measured using a suture retention test and a ultimate tensile strength (UTS) test.

ICL was inverted and stretched over a pair of mandrels which were inserted into an ICL mounting frame. Mandrels were of stainless steel tubing with an external diameter of 4.75 mm. The ICL and mandrels were then placed in a dehydration chamber set at 20% relative humidity at 4° C. for about 60 minutes. After dehydration, the ICL was removed from the chamber and the mandrels. The lymphatic tag areas were removed and the ICL was manually wrapped around the mandrel twice to form an 'unwelded' bilayer construct. The wrapped ICL was returned to the dehydration chamber and allowed to dry for another 90 minutes still at 20% relative humidity to about 50% moisture +/−10%. To determine the amount of moisture present in a sample construct, a CEM™ oven was used.

A THERMOCENTER™ oven was set for the designated temperature treatment for the constructs to be welded. Temperatures tested for welding ranged from 55° to 70° C. Once the constructs were placed in the oven, the oven was allowed to equilibrate before timing began. The constructs were allowed to remain in the chamber for the time required for that condition. Welding times ranged from 7 to 30 minutes. As soon as the time was completed the constructs were removed from the chamber and placed in a 4° C. water bath for about 2 to 5 minutes. The welded constructs were then returned to the dehydration chamber for about 30 minutes until dehydrated to about 20% +/−10%.

After dehydration, constructs were inserted into a vessel containing EDC in either deionized water or deionized water and acetone at the concentrations appropriate for the conditions tested. EDC concentrations tested were 50, 100, and 200 mM. Acetone concentrations tested were 0, 50, and 90% in water. The time duration for crosslinking was determined by the conditions tested. Crosslinking times were 6, 12, and 24 hours. After crosslinking, the construct was removed from the solution and rinsed with physiological pH phosphate buffered saline (PBS) three times at room temperature. The welded and crosslinked construct was then removed from the mandrel and stored in PBS until testing. In addition to the thirty constructs that were prepared, two other bilayer constructs were prepared by welding at 62° C. for 15 minutes and crosslinked in 100 mM EDC in 100% $H_2O$ for 18 hours.

The suture retention test was used to determine the ability of a construct to hold a suture. A piece of construct was secured in a CHATTILION™ force measurement device and 1–2 mm bite was taken with a SURGLENE™ 6–0 suture, pulled through one wall of the construct and secured. The device then pulls at the suture to determine the force required to tear the construct material. The average suture breaks between 400–500 g of force; the surgeons pull tends to be 150 g of force.

The weld/material strength test was performed to determine the UTS of a construct. Sample rings of 5 mm lengths were excised from each tube and each was tested for their ultimate tensile strength (UTS) test using a mechanical testing system MTS™. Three sample rings were excised from each tube for three test pulls done for each construct for a total of 90 pulls. A ring was placed in the grips of the MTS™ and is pulled at a rate of 0.02 $kg_{force}$/sec until the weld slips or breaks, or until the material (rather than the weld) breaks.

Example 3

Various Welding Temperatures of ICL

The effect of welding temperature and quenching after welding on weld strength were examined for the ICL two layered tube application.

An ICL sample of 10 feet long was cut along its length and prepared as in the procedure outlined in Example 2. Six 6 mm diameter tubes ranging between 15–20 cm in length were prepared for each temperature condition.

Tubes were subjected to a temperature condition while wet for 3.5 hours. Temperatures conditions were: Room temperature (20° C.), 55° C., 62° C. and 62° C. then immediately quenched in 4° C. bath for one minute. All tubes were then crosslinked in EDC. Six tubes were placed together in 300 mL 100 mM EDC overnight at room temperature. Tubes were then rinsed with physiological strength phosphate buffered saline after crosslinking.

Sample rings of 5 mm lengths were excised from each tube and each was tested for ultimate tensile strength (UTS) test using a MTS™. Five sample rings were taken from each tube for 5 test pulls on each of 6 tubes per condition for a total of 30 pulls.

Weld strength was less consistent for tubes bonded by dehydration at room temperature as compared to the other temperature treatments when tested using the UTS test. One of the six tubes welded at room temperature had UTS measurements comparable to those of the other treatments. For the tubes welded at other temperatures either with or without quenching, there were no differences in weld strength. After UTS testing, it was determined that the breaking of the material was not a separation of the weld but a material failure in all instances.

Example 4

The Antigenicity of Crosslinked Intestinal Collagen Layer

Fresh samples of porcine submucosal intestinal layer were obtained after the cleaning step as described in example 1. Samples were then left untreated and stored in water, soaked in physiological strength phosphate buffered saline, treated with 0.1% peracetic acid, or were treated with 0.1% peracetic acid and then crosslinked with 1-ethyl-3-(3-dimethylaminopropyl) carbodiimide hydrochloride (EDC). Samples were then extracted with a solution of 0.5 M NaCl/0.1 M tartaric acid for about 18 hours.

Two 12% Tris-glycine sodium dodecylsulfate-polyacrylamide gels (Novex Precast Gels cat# EC6009) were run and then transferred after about 18 hours to 0.45 µ nitrocellulose paper. Tartaric acid extracts of either untreated or treated ICL were run against a control standard lane containing: 10 µd Kaleidoscope Prestained Standards (Bio-Rad cat# 161-0324): 2 µl biotinylated SDS-PAGE low range molecular weight standards (Bio-Rad cat# 161-0306): 6 µl loading buffer; 10 µd of control standard were loaded to each lane. The gel was blotted for about 2 hours with 1% dry non-fat milk (Carnation) in phosphate buffered saline. The gel was then washed three times with borate buffered saline/Tween with 200 µl of wash per lane. Primary antibody in 200 µl of Rb serum and borate buffered saline (100 mM boric acid: 25 mM sodium borate: 150 mM NaCl)Tween was added to each lane at various titer range (1:40, 1:160, 1:640 and 1:2560). The gel was then incubated at room temperature for one hour on a rocker platform (Bellco Biotechnology) with the speed set at 10. The gel was then washed again three times with borate buffered saline/Tween. Secondary antibody, goat anti-rabbit Ig-AP (Southern Biotechnology Associates Inc. cat# 4010-04) at a 1:1000 dilution was added to the lanes at 200 µl per lane and the gel was incubated for one hour at room temperature on a rocker platform. The nitrocellulose membrane was then immersed in AP color development solution while incubated at room temperature on a rocker platform until color development was complete. Development was stopped by washing the membrane in deionized water for ten minutes on a rocker platform while changing the water once during the ten minutes. The membrane was then air dried.

The results obtained from analysis of the gel suggest that the antigenicity of the porcine derived ICL treated with peracetic acid and EDC has greatly reduced antigenicity as compared to the other treatments.

Example 5

Six Layered Tissue Repair Fabric as an Abdominal Wall Patch

Six layers of porcine intestinal collagen were superimposed onto one another on a glass plate. A second plate of glass was then placed on top of the intestinal collagen layers and clamped tightly to the first plate. The apparatus was placed into a conventional type oven at 62° C. for one hour. Immediately following heating, the apparatus was placed into a 4° C. water bath for ten minutes. The apparatus was disassembled, the intestinal collagen layers removed, and treated with 100 mM 1-ethyl-3-(3-dimethylaminopropyl) carbodiimide hydrochloride (EDC) in 50% acetone for four hours at 25° C. The material was bagged and sterlized by gamma irradiation (2.5 Mrad).

The tissue repair fabric was sutured in a 3 cm×5 cm defect in the midline of New Zealand White rabbits (4 kg) using a continuous 2–0 prolene suture. Animals were sacrificed at four weeks, ten weeks, and 16 weeks, and examined grossly, mechanically, and histologically. Gross examination showed minimal inflammation and swelling. The graft was covered with a glistening tissue layer which appeared to be continuous with the parietal peritoneum. Small blood vessels could be seen proceeding circumferentially from the periphery to the center of the patch. Mechanically the graft was stable with no reherniation observed. Histological examination revealed relatively few inflammatory cells and those that were observed were primarily near the margin of the graft (due to the presence of prolene suture material). The peritoneal surface was smooth and covered entirely by mesothelium.

Example 6

Two Layered Tissue Repair Fabric as a Pericardial Repair Patch

Two layers of porcine intestinal collagen were superimposed onto one another on a glass plate. A second plate of glass was then placed on top of the intestinal collagen layers and clamped tightly to the first plate. The apparatus was placed into a conventional type oven at 62° C. for one hour. Immediately following heating, the apparatus was placed into a 4° C. water bath for ten minutes. The apparatus was disassembled, the intestinal collagen layers removed, and treated with 10 mM 1-ethyl-3-(3-dimethylaminopropyl) carbodiimide hydrochloride (EDC) in 50% acetone for four hours at 25° C. The material was bagged and sterilized by gamma irradiation (2.5 Mrad).

A 3×3 cm portion of New Zealand white rabbit pericardium was excised and replaced with a same size piece of tissue repair fabric (anastomosed with interrupted sutures of 7–0 prolene). Animals were sacrificed at four weeks and at 180 days, examined grossly, mechanically, and histologically. Gross examination showed minimal inflammation and swelling. Small blood vessels could be seen proceeding circumferentially from the periphery to the center to the graft. Mechanically, the graft was stable without adhesion to either the sternum or pericardial tissue. Histological examination revealed relatively few inflammatory cells and those that were observed were primarily near the margin of the graft (due to the presence of prolene suture material).

Example 7

Hernia Repair Device

A prototype device for hernia repair was developed using ICL to have a hollow inner region. The device, when completed, had a round conformation bonded at the periphery and a swollen inner region rendered swollen by the inclusion of physiological strength phosphate buffered saline. The inner region can optionally accommodate a wire coil for added rigidity or other substance for structural support or delivery of substance.

To assemble ICL multilayer sheets, 15 cm lengths of ICL were trimmed of lymphatic tags and cut down the side with the tags to form a sheet. Sheets were patted dry with Texwipes. On a clean glass plate (6"×8"), sheets were layered mucosal side down. In this case, two two-layer and two four-layer patches were constructed by layering either two or four layers of ICL on the glass plates. A second glass plate (6"×8") was placed on top of the last ICL layer and the plates were clamped together and then placed in a hydrated oven at 62° C. for one hour. Constructs were then quenched in deionized water at 4° C. for about ten minutes. The glass plates were then removed from the bath and a plate removed from each patch. The now bonded ICL layers were then smoothed out to remove any creases or bubbles. The glass plate was replaced upon the ICL layers and returned to the hydrated oven for 30–60 minutes until dry. Patches were removed from the oven and partially rehydrated by spraying with physiological strength phosphate buffered saline.

For the construction of a bi-layer construct, one bi-layer patch was removed from the glass plates and placed upon the other bi-layer patch still on the other glass plate. An annular plate ($d_{out}$=8.75 cm; $d_{in}$=6 cm) was placed upon the second patch. About 10 cc of physiological strength phosphate buffered saline was then injected through a 25 gauge needle between the two bilayer patches. A second glass plate was then placed on top of the annular plate and were then clamped together. For the construction of a four-layer construct, the same steps were followed except that two four-layer patches were used rather than two bi-layer patches. The constructs were placed in a hydrated oven at 62° C. for one hour. Constructs were then quenched in deionized water at 4° C. for about fifteen minutes. Constructs were then crosslinked in 200 mL 100 mM EDC in 50% acetone for about 18 hours and then rinsed with deionized water. The constructs were then trimmed to shape with a razor blade to the size of the outer edge of the annular plate.

Example 8

Intervertebral Disc Replacement

ICL, dense fibrillar collagen and hyaluronic acid were configured to closely approximate the anatomic structure and composition of an intervertebral disc.

Dense fibrillar collagen diskettes containing hyaluronic acid were prepared. 9 mg hyaluronic acid sodium salt derived from bovine trachea (Sigma) was dissolved in 3 mL 0.5 N acetic acid. 15 mL of 5 mg/mL collagen (Antek) was added and mixed. The mixture was centrifuged to remove air bubbles. To ,three transwells (Costar) in a six well plate (Costar) was added 5 mL of the solution. To the area outside the transwell was added N600 PEG to cover the bottom of the membranes. The plate was maintained at 4° C. on an orbital shaker table at low speed for about 22 hours with one exchange of PEG solution after 5.5 hours. PEG solution was removed and the transwells dehydrated at 4° C./20% Rh overnight.

To assemble ICL multilayer sheets, 15 cm lengths of ICL were trimmed of lymph tags and cut down the side with the tags to form a sheet. Sheets were patted dry with Texwipes. On a clean glass plate, sheets were layered mucosal side down to five layers thick and a second glass plate was laid on top of the fifth layer. Five five-layer patches were constructed. The plates with the ICL between were clamped together and placed in a hydrated oven at 62° C. for one hour. Constructs were then quenched in RODI water at 4° C. for about ten minutes then were removed form the quench bath and stored at 4° C. until assembly of the disc.

To another glass plate, one large patch was laid. A slightly smaller patch was laid upon the first patch aligned to one edge of the larger patch. One patch was cut in half and a hole was cut in the center of each approximating the size of the DFC diskettes. With the center holes aligned, the two halves were laid upon the second patch aligned to the same edge. Three rehydrated DFC/HA diskettes were placed within the center hole. Another slightly smaller patch was laid upon the two halves containing the DFC diskettes and a larger patch laid upon the smaller patch, both aligned to the same edge. A second glass plate was placed on top of the construct. The resultant shape was that of a wedge with the thicker side being the one with the aligned edges tapering to the opposite side. The thus formed device was placed in a hydrated oven at 62° C. for one hour and then quenched in RODI water at 4° C. for about ten minutes. The device was then crosslinked in 100 mM EDC (Sigma) in 90% acetone (Baxter) for about five hours and then rinsed with three exchanges of phosphate buffered saline. The edges of the device were then trimmed with a razor blade.

Example 9

The Formation of Vascular Graft Construct

The proximal jejunum of a pig was harvested and processed with a Gut Cleaning Machine (Bitterling, Nottingham, UK) and then decontaminated with peracetic acid solution as described in example 1. The peracetic acid treated ICL (PA-ICL) was cut open longitudinally and lymphatic tag areas were removed to form a sheet of ICL. The ICL sheets were wrapped around a 6.0 mm diameter stainless steel mandrels to form bilayer constructs. The constructs (on mandrels) were then placed in an equilibrated THERMOCENTER™ oven chamber set at 62° C. for about 1 hour. The constructs were removed from the chamber and placed in a 4° C. water bath for about 2 to 5 minutes. The constructs were chemically crosslinked in 50 mL of 100 mM 1-ethyl-3-(3-dimethylaminopropyl) carbodiimide (EDC) in 50/50 water/acetone solution for 18 hours to form peracetic acid treated, EDC crosslinked (PA/EDC-ICL) vascular graft constructs. The constructs were removed from the mandrels and rinsed with water to remove residual EDC solution.

After removal from the mandrels, a layer (approximately 200 μm thick) of type I collagen extracted from bovine tendon, was deposited on the luminal surface of the constructs according to the method described in U.S. Pat. No. 5,256,418, incorporated herein. Polycarbonate barbs (luer lock fittings that are conically shaped on one end) were sealably fixed at either end of the constructs and the constructs were placed horizontally in a deposition fixture. A 50 mL reservoir of 2.5 mg/mL acid-extracted collagen, prepared by the method described in U.S. Pat. No. 5,106,949, incorporated herein, was attached via the barbs. The collagen was allowed to fill the lumen of the ICL tube and was then placed into a stirring bath of 20% MW 8000 polyethylene glycol (Sigma Chemicals Co.) for 16 hours at 4° C. The apparatus was then dismantled and a 4 mm diameter glass rod was placed into the collagen-filled ICL tube to fix the luminal diameter. The prosthesis was then allowed to dry.

The luminal DFC layer was coated with benzalkonium chloride heparin (HBAC) by dipping the grafts three times into an 800 U/mL solution of HBAC and allowed to dry. Finally, the graft received a final chemical sterilization treatment in 0.1% v/v peracetic acid. The graft was stored in a dry state until the implant procedure.

Example 10

Implant Studies on Animal Models

Twenty-five mongrel dogs weighing 15–25 kg were fasted overnight and then anesthetized with intravenous thiopental (30 mg/kg), entubated, and maintained with halothane and nitrous oxide. Cefazolin (1000 mg) was administered intravenously preoperatively as well as postoperatively. Each dog received either an aortic bypass grafts or a femoral interposition graft. For the aortic bypass grafts, a midline abdominal incision was made and the aorta exposed from the renal arteries to the bifurcation, followed by the administration of intravenous heparin (100 U/kg). The grafts (6 mm×8 cm) were, placed between the distal infrarenal aorta (end-to-side anastomosis) and the aorta just proximal to the bifurcations (end-to-side anastomosis). The aorta was ligated distal to the proximal anastomosis. The incisions were closed and the dogs maintained on aspirin for 30 days post surgery. For the femoral interposition grafts, the animals were opened bilaterally, the femoral arteries exposed, and a 5 cm length excised. The grafts (4 mm×5 cm) were anastomosed in end-to-end fashion to the femoral artery. On the contralateral side, a control graft was placed. The incisions were closed and the animals were maintained on aspirin for 30 days post surgery. Post operative follow-up ranged from 30 days to 360 days. Pre-implant, and four and eight weeks post-implant bloods were collected. Animals were sacrificed at various time points (30 days, 60 days, 90 days, 180 days, and 360 days).

New Zealand White rabbits weighing 3.5–4.5 kg were fasted overnight, and then anesthetized with acepromazine (20 mg) and ketamine (40 mg), entubated, and maintained with ketamine (50 mg/mL), injected intravenously as needed. Penicillin (60,000 U) was administered intramuscularly preoperatively. A midline abdominal incision was made and the aorta exposed from the renal arteries to the bifurcation, followed by the administration of intravenous heparin (100 U/kg). A 3 cm length of aorta was excised, and the grafts (2.5 mm×3 cm) were anastomosed in end-to-end fashion to the aorta. The incisions were closed and the animals were maintained with no anticoagulant therapy post surgery. Post operative follow-up ranged from 30 days to 360 days. Animals were sacrificed at various time points (30 days, 60 days, 90 days, 180 days, and 360 days).

The implants along with adjacent vascular tissues obtained from sacrificed animals were fixed for transmission electron microscopy (TEM) analysis for 4 hr in a solution of 2.0% paraformaldehyde, 2.5% glutaraldehyde in 0.1 M sodium cacodylate, pH 7.4. Samples were then post-fixed in 1.0% OsO4 (in 0.1M sodium cacodylate) and stained en bloc with 2.0% uranyl acetate (aqueous). After secondary fixation all specimens were dehydrated in a graded ethanol series and propylene oxide and embedded in Epox 812 (Ernest F. Fullam, Rochester, N.Y., USA). Ultrathin (~700 nm) sections were stained with uranyl acetate and lead citrate. Sections were examined on a JEOL Instruments JEM100S at 80 kV. For scanning electron microscopy (SEM), samples were fixed for 18 hr in half strength Karnovsky's solution and rinsed five times in Sorensen's phosphate buffer prior to post fixation in 1.0% OsO4 for 1 hr. Samples were then rinsed twice in Sorensen's phosphate buffer and three times in double distilled water. Dehydration was accomplished through an ethanol series (50%, 70%, 90%, and 100%), followed by critical point drying. Samples were mounted and coated with 60/40 gold/palladium.

ICL graft explants from dogs and rabbits were examined histologically to evaluate host cell ingrowth. Masson's trichrome staining of a 60 day explant showed significant host infiltrate. The darker blue staining showed collagen of the ICL while matrix surrounding the myofibroblasts, stained lighter blue, showed an abundance of host collagen. High power magnification of the section showed numerous cells intermingled within the ICL. The inflammatory response seen at 30 days had been resolved and the cellular response was predominantly myofibroblastic. The surface of the remodeled graft was lined by endothelial cells as demonstrated by SEM and Factor VIII staining. By 360 days, a mature 'neo-artery' had been formed. The neo-adventitia was composed of host collagen bundles populated by fibroblast-like cells. The cells and matrices of the remodeled construct appeared quite mature and tissue-like.

Example 11

Generation of Anti-ICL Antibodies

Fresh samples of porcine submucosal intestinal layer were obtained after the cleaning step as described in example 1 but were not peracetic acid treated. Samples were then left untreated (NC-ICL), treated with 0.1% peracetic acid (PA-ICL), or treated with 0.1% peracetic acid and then crosslinked with 1-ethyl-3-(3-dimethylaminopropyl) carbodiimide hydrochloride (PA/EDC-ICL).

New Zealand White rabbits were immunized with 0.5 mg of any one of the three types of ICL samples (NC-ICL, PA-ICL, or PA/EDC-ICL) to generate anti-serum. Initially, rabbits were injected subcutaneously with 0.5 mL of homogenized untreated ICL ini Freund's complete adjuvant (1:1, 1 mg/mL). Sham rabbits received 0.5 mL of phosphate buffered saline in Freund's complete adjuvant. Rabbits were boosted every 3 to 4 months with 0.5 mL of the appropriate form of ICL in Freund's incomplete adjuvant (0.25 mg/mL). Sera were collected 10–14 days after each boost.

Example 12

Generation of ICL Extracts and Characterization of Potentially Antigenic Proteins Associated with Native Collagen Proteins were extracted from NC-ICL, PA-ICL, or PA/EDC-ICL using tartaric acid (Bellon, G., et al (1988) Anal. Biochem. 175: 263–273) or TRITON X-100 (Rohm and Haas). Pulverized NC-ICL, PA-ICL, or PA/EDC-ICL (10% w/v) were mixed with either tartaric acid (0.1 M tartaric acid, 0.5 M NaCl) or TRITON X-100 (Rohm and Haas) extraction buffer (TEB; 1% TRITON X-100 in 20 mM Tris HCl (pH 7.2), 2 mM EGTA, 2 mM EDTA, 1 mM phenylmethylsulfonyl fluoride, and 25 mg/mL each of aprotinin, leupeptin, and pepstatin (Sigma, St. Louis, Mo.)). The mixtures were incubated overnight at 4° C. The extracts were gauze filtered to remove debris, dialyzed against PBS and concentrated using Centriprep-30 (Amicon, Danvers, Mass.). Extracts were stored at –80° C. until used.

Tartaric acid and TEB extracts were separated on 10% polyacrylamide gels by SDS-PAGE according to Laemnili (Laemnili, U.K. (1970) Nature 227: 680–685). Gels were either silver stained (Bio-Rad, Hercules, CA) or transferred to nitrocellulose membranes (Amersham, Arlington Heights, Ill.). Multiple protein bands were visualized in the NC-ICL extracts by silver staining. In contrast, only two bands were visible in the PA-ICL extracts and no protein bands were seen in the lanes containing PAIEDC-ICL. These results suggest that peracetic acid and EDC treatment, in combination, leads to a decrease in the extractable non-collagenous proteins in ICL.

Immunoblot transfer was done overnight using a Trans-Blot Cell (Bio-Rad) in Tris-Glycine 20% methanol transfer buffer. Nitrocellulose membranes containing ICL transferred proteins were blocked with Blotto buffer (1% non-fat dry milk in borate buffered saline with 0.1% Tween-20 (BBS/Tween)) for one hour at room temperature. The nitrocellulose membranes were transferred to a multiscreen apparatus containing 12 individual lanes. The membranes were washed three times with BBS/Tween. Positive control or test sera (100 μL/lane) were added to the membrane and rocked at room temperature for 1 hour. Each lane was washed three times with BBS/Tween. Secondary antibodies: ALPH-labeled goat anti-rabbit Ig or ALPH-labeled goat anti-dog Ig (Southern Biotechnology) were added to the appropriate lanes (100 μL/lane) and streptavidin-AP (100 μL) was added to one of the lanes containing the Kaleidoscope molecular weight standards (Bio-Rad). An alkaline phosphatase conjugate substrate kit (Bio-Rad) was used to visualize the immunoblots.

Rabbit anti-NC-ICL serum, generated by repeated immunization with NC-ICL, was used to detect potentially immunoreactive proteins. Sera from immunized rabbits recognized antigens with molecular weights in the range of <30, 40–70, and >100 kDa in the tartaric acid extract. These same sera were tested on immunoblots of TEB extracts from NC-ICL. Immunoreactive proteins were detected with molecular weights ranges similar to those detected in the tartaric acid extract, with additional reactivity detected in the 70–100 kDa range. The results indicated that NC-ICL contains multiple proteins which are immunoreactive and these proteins can be extracted by tartaric acid or TEB. The greater number of immunoreactive proteins present in the TEB extract correlated with the increase in proteins extracted using TEB as compared to tartaric acid.

Example 13

Effect of PA or EDC Treatment of ICL on the Antigenicity of Type I Collagen in ICL Sera from rabbits immunized with NC-ICL, PA-ICL, or PA/EDC-ICL (sera prepared as described in example 11) or acid extracted type I collagen (Organogenesis, Canton, Mass.) were tested for type I collagen specific antibodies by ELISA. ELISA plates (Immulon II, NUNC, Bridgeport, N.J.) were coated with 200 mL/well of 1 mg/mL acid extracted type I collagen in 0.05 M carbonate buffer (pH 9.6) overnight at 4° C. Plates were washed twice with PBS/Tween-20 (0.1%). Serum samples from animals or rabbit anti-collagen type I antibody (Southern Biotechnology, Birmingham, Ala.) were added to wells (100 mL/well) and incubated for 1 hr at room temperature. Plates were washed three times with PBS/Tween. Secondary antibodies: ALPH-labeled goat anti-rabbit Ig or ALPH-labeled goat anti-dog Ig (Southern Biotechnology) were added to the appropriate wells and incubated at room temperature for 1 hour. Plates were washed three times with PBS/Tween. P-nitrophenylphosphate (PNPP) substrate (1 mg/mL) was added to each well (100 mL/well). Absorbance was read at 405 nm on a SpectraMax microplate reader (Molecular Devices, Sunnydale, Calif.).

Anti-collagen type I antibodies could not be detected in sera from rabbits immunized with any form of ICL, even at a 1:40 serum dilution. In contrast, rabbits immunized with purified type I collagen had antibody titer of 1:2560. These data suggest that crosslinking is not necessary to reduce the antigenicity to collagen type I, since rabbits immunized with NC-ICL did not generate anti-collagen type I antibodies. These data thus suggest that the immunodominant proteins in NC-ICL are non-collagenous proteins. Also, the effect of PA and EDC on reducing the antigenicity of ICL is directed toward the non-collagenous proteins.

Example 14

Effects of Disinfecting and Crosslinking on Antigenicity of ICL

The effect of PA and EDC treatment on the antigenicity of ICL was determined by using anti-NC-ICL antiserum to probe for immunoreactive proteins present in tartaric acid or TEB extracts of PA or PA/EDC treated ICL.

Tartaric acid extracts of PA-ICL and TEB extracts of PA/EDC-ICL were separated on 10% SDS-PAGE gels and transferred to nitrocellulose membranes for immunoblot analysis, as described in Example 12. NC-ICL specific antisera were used to probe for immunoreactive proteins in each extract. Even when immunoblots of PA-ICL. and PA/EDC-ICL were overexposed, no reactivity could be detected in lanes containing anti-NC-ICL antibodies thus suggesting that the immunoreactive proteins detected in the NC-ICL are either missing or their epitopes have been modified such that they are no longer recognized by anti-NC-ICL anti-serum. To address this latter issue, serum from rabbits immunized with either PA-ICL or PA/EDC-ICL was also tested. No antibody binding was detected in any of the lanes above background. These data indicate that even when rabbits were immunized with modified ICL they did not generate antibodies which could recognize modified ICL extracted proteins. These results suggest that the proteins removed or modified during the process of disinfecting and crosslinking are the same proteins responsible for the antigenicity of NC-ICL.

Antibody response of PA-ICL or PA/EDC-ICL immunized rabbits was analyzed by immunoblotting, as described in Example 12. This approach was taken to ensure that the lack of reactivity of anti-NC-ICL sera with PA/EDC-ICL was due to the absence of proteins in ICL and not due to an inability to extract proteins which might be accessible to the immune system in vivo since crosslinking of collagenous materials with EDC could reduce the quantity and quality of protein extracted from ICL. Anti-ICL antisera was generated using PA-ICL or PA/EDC-ICL to immunize rabbits. Sera from these rabbits were tested for antibodies specific for proteins in either tartaric acid or TEB protein extracts of NC-ICL. Anti-PA-ICL recognized the 207, 170, and 38–24 kDa proteins recognized by anti-NC-ICL, but lost reactivity to the lower molecular weight proteins. No bands were detected by the anti-PA/EDC-ICL serum from 1 rabbit. Serum from another anti-PAIEDC-ICL rabbit reacted with the 24–38 kDa proteins. These data suggested that both PA-ICL and PA/EDC-ICL are less antigenic than NC-ICL. Either the antigenic epitopes of ICL are removed during the disinfecting and crosslinking process or they are modified to reduce their antigenicity. In either case, disinfection and crosslinking resulted in a material whose antigenicity was significantly reduced.

Example 15

Determination of Humoral Immune Response in Graft Recipients

Dogs were tested for a humoral immune response to ICL graft components to determine if ICL must retain its antigenicity to stimulate cell ingrowth into the graft. Pre-implant, and four and eight weeks post-implant blood samples were collected from fifteen dogs that received PAIEDC-ICL vascular grafts. Serum from each blood sample was tested for antibodies to proteins in both the tartaric acid and TEB extracts of NC-ICL. Even at a 1:40 dilution of serum, none of the dogs tested had antibodies which reacted with ICL proteins. These same serum samples were tested for the presence of anti-collagen type I antibodies by ELISA. All serum samples were negative for antibodies to type I collagen at a serum dilution of 1:40.

Masson's trichrome staining of explant paraffin sections from these dogs did shown infiltration of host cells. These results demonstrate that PA/EDC-ICL does not elicit an antibody response when the host is actively remodeling the material.

Although the foregoing invention has been described in some detail by way of illustration and example for purposes of clarity and understanding, it will be obvious to one of skill in the art that certain changes and modifications may be practiced within the scope of the appended claims.

What is claimed:

1. A prosthesis comprising two or more superimposed, bonded layers of collagenous tissue which have been crosslinked with a crosslinking agent that permits bioremodeling, wherein said collagenous tissue is derived from tunica submucosa of the small intestine separated from the other layers of the small intestine, wherein the prosthesis is non-antigenic, wherein the prosthesis is sterilized, wherein the two or more layers of the prosthesis are completely bioremodelable, and which, when implanted into a mammalian patient, undergoes controlled biodegradation occurring with adequate living cell replacement such that the original implanted prosthesis is remodeled by the patient's living cells.

2. The prosthesis of claim 1 wherein the shape of said prosthesis is flat, tubular, or complex.

3. The prosthesis of claim 1 wherein said collagenous layers are bonded together by heat welding for a time and under conditions sufficient to effect the bonding of the collagenous tissue layers.

4. The prosthesis of claim 1 wherein said prosthesis is crosslinked with the crosslinking agent 1-ethyl-3-(3-dimethylaminopropyl) carbodiimide hydrochloride.

5. The prosthesis of claim 4 wherein sulfo-N-hydroxysuccinimide is added to the crosslinking agent.

6. The prosthesis of claim 4 wherein acetone is added to the crosslinking agent.

7. The prosthesis of claim 1 wherein the prosthesis is sterilized with peracetic acid.

8. The prosthesis of claim 1, wherein the prosthesis has one or more surfaces and wherein the one or more surfaces of said prosthesis is coated with a collagenous material which acts as a smooth flow surface.

9. The prosthesis of claim 1 wherein said prosthesis further contains pores.

10. The prosthesis of claim 1 wherein said prosthesis is further composed of chopped collagen fibers.

11. The prosthesis of claim 1 wherein said prosthesis is further composed of collagen threads.

12. The prosthesis of claim 11 wherein said collagen threads are arranged to form a felt, a bundle, a wave or a braid.

13. The prosthesis of any claims 10–12 wherein said collagen fibers or threads are partially or completely crosslinked.

14. The prosthesis of claim 1 wherein said prosthesis additionally contains an anticoagulant, one or more antibiotics, or one or more growth factors.

15. A method for preparing a prosthesis having two or more superimposed, bonded layers of collagenous tissue, comprising:
    (a) bonding two or more collagen layers together using heat welding by heating said collagenous layers for a time and under conditions sufficient to effect the bonding of the collagen layers and to form a prosthesis;
    (b) cooling said heated prosthesis; and
    (c) crosslinking said prosthesis with a crosslinking agent that permits bioremodeling, wherein said collagenous tissue is derived from tunica submucosa of the small intestine separated from the other layers of the small intestine, wherein said thus formed prosthesis is non-antigenic, and wherein said thus formed prosthesis when implanted into a mammalian patient, undergoes controlled biodegradation occurring with adequate living cell replacement such that the original implanted prosthesis is remodeled by the patient's living cells;
wherein the collagenous tissue layers are sterilized with peracetic acid before bonding in step (a) or the prosthesis is sterilized after crosslinking in step (c).

16. The method of claim 15 wherein said heat welding is from about 50° C. to about 75° C.

17. The method of claim 15 wherein said cooling is accomplished by quenching.

18. The method of claim 15 wherein said heat welding is accomplished for a time from about 7 minutes to about 24 hours.

19. The method of claim 15 wherein said prosthesis is crosslinked with the crosslinking agent 1-ethyl-3-(3-dimethylaminopropyl) carbodiimide hydrochloride.

20. The method of claim 15 wherein said heat welding is from about 60° C. to about 65° C.

21. The method of claim 15 wherein said heat welding is at about 62° C.

22. The method of claim 15 wherein said heat welding is accomplished for a time of about 1 hour.

23. A method of repairing or replacing a damaged tissue comprising implanting a non-antigenic prosthesis in a patient comprising two or more superimposed, bonded layers of collagenous tissue derived from tunica submucosa of the small intestine separated from the other layers of the small intestine which have been sterilized with peracetic acid and crosslinked with a crosslinking agent that permits bioremodeling, wherein two or more layers of the prosthesis are completely bioremodelable, and which, when implanted into a mammalian patient, undergoes controlled biodegradation occurring with adequate living cell replacement such that the original implanted prosthesis is remodeled by the patient's living cells.

24. A method for preparing a non-antigenic prosthesis prepared from collagenous tissue derived from tunica submucosa of the small intestine separated from the other layers of the small intestine comprising:
    (a) sterilizing the collagenous tissue with peracetic acid at a concentration between about 0.01 and 0.3% in water; and
    (b) crosslinking said sterilized collagenous tissue with a crosslinking agent that permits bioremodeling;
wherein a prosthesis is formed from two or more superimposed, bonded layers of collagenous tissue, wherein two or more layers of the prosthesis are bioremodelable, and wherein the prosthesis when implanted into a mammalian patient, undergoes controlled bioremodeling occurring with adequate living cell replacement such that the original implanted prosthesis is remodeled by the patient's living cells without eliciting a significant humoral immune response.

25. The method of claim 24 wherein the prosthesis is sterilized with peracetic acid prior to implantation into the mammalian patient.

* * * * *